US00PP11274P

United States Patent [19]

van Rijn

[11] Patent Number: Plant 11,274

[45] Date of Patent: Mar. 7, 2000

[54] BOUGAINVILLEA PLANT NAMED 'VERA LIGHT PURPLE'

[75] Inventor: Magdalena J. M. van Rijn, Schipluiden, Netherlands

[73] Assignee: Rijnplant, Schipluiden, Netherlands

[21] Appl. No.: 08/959,903

[22] Filed: Oct. 29, 1997

[51] Int. Cl.[7] ..... A01H 5/00

[52] U.S. Cl. ..... Plt./256

[58] Field of Search ..... Plt./67.7, 256

[56] References Cited

U.S. PATENT DOCUMENTS

P.P. 2,630 5/1966 Barry, Jr. ..... Plt./67.7
P.P. 3,630 10/1974 Thingholm ..... Plt./67.7

*Primary Examiner*—Douglas W. Robinson
*Assistant Examiner*—Kent L. Bell
*Attorney, Agent, or Firm*—C. A. Whealy

[57] ABSTRACT

A distinct cultivar of Bougainvillea plant named 'Vera Light Purple', characterized by its compact and upright growth habit; moderate to rapid growth rate; thornless stems; light purple/dark pink flowers bracts; and spherical inflorescences with numerous flowers.

2 Drawing Sheets

The present invention relates to a new and distinct cultivar of Bougainvillea plant, botanically known as *Bougainvillea spectabilis,* and hereinafter referred to by the cultivar name 'Vera Light Purple'.

The new Bougainvillea is a product of a planned breeding program conducted by the inventor in Schipluiden, The Netherlands. The objective of the breeding program was to create new Bougainvillea cultivars having spherical inflorescences, compact plant habit and long-lasting flowers.

The new Bougainvillea originated from a cross made by the inventor of two of the inventor's proprietary *Bougainvillea spectabilis* seedling selections. The cultivar 'Vera Light Purple' was discovered and selected by the inventor in May, 1993, as a flowering plant within the progeny of this cross in a controlled environment in Schipluiden, The Netherlands.

Asexual reproduction of the new Bougainvillea by terminal cuttings taken at Schipluiden, The Netherlands, has shown that the unique features of this new Bougainvillea are stable and reproduced true to type in successive generations.

The following traits have been repeatedly observed and are determined to be the unique characteristics of 'Vera Light Purple'. These characteristics in combination distinguish 'Vera Light Purple' as a new and distinct cultivar:

1. Upright and compact growth habit.
2. Moderate to rapid growth rate.
3. Thornless stems.
4. Light purple/dark pink flower bracts.
5. Spherical inflorescences with numerous flowers.

The new Bougainvillea has not been observed under all possible environmental conditions. The phenotype may vary somewhat with variations in environment such as temperature and light intensity, without, however, any variance in genotype.

Plants of the new Bougainvillea are similar to plants of the nonpatented Bougainvillea cultivar 'Alexander'. However, in side-by-side comparisons conducted in Schipluiden, The Netherlands, plants of the new Bougainvillea were more compact, grew faster, and were more floriferous. In addition, plants of the new Bougainvillea had spherical inflorescences whereas plants of the cultivar 'Alexander' do not form spherical inflorescences.

Plants of the new Bougainvillea can also be compared to plants of its daughter cultivar, 'Rpboug 327', disclosed in U.S. Plant Patent application Ser. No. 08/959,904. However, in side-by-side comparisons conducted in Schipluiden, The Netherlands, plants of the new Bougainvillea had lighter purple flower bracts, fewer flowers per inflorescence, and slightly larger flowers than plants of 'Rpboug 327'.

The accompanying colored photographs illustate the overall appearance of the new cultivar, showing the colors as true as it is reasonably possible to obtain in colored reproductions of this type.

On the first sheet, the top photograph comprises a top perspective view of a typical plant of 'Vera Light Purple'.

The bottom photograph on the first sheet comprises a top perspective view of a typical inflorescence of 'Vera Light Purple'.

The photograph on the second sheet comprises a close-up view of typical flowers of 'Vera Light Purple'. The flower and foliage colors in these photographs may appear different than the actual colors due to light reflectance.

In the following description, color references are made to The Royal Horticultural Society Colour Chart except where general terms of ordinary dictionary significance are used. The following observations and measurements describe plants grown in 13-cm containers in Schipluiden, The Netherlands, in a glass-covered greenhouse with day temperatures ranging from 16 to 35° C. and minimum night temperatures of 15° C.

Botanical classification: *Bougainvillea spectabilis* cultivar 'Vera Light Purple'.

Parentage:

*Male, or pollen, parent.*—Inventor's proprietary seedling selection of *Bougainvillea spectabilis.*

*Female, or seed, parent.*—Inventor's proprietary seedling selection of *Bougainvillea spectabilis.*

Propagation:

*Type.*—Terminal cuttings.

*Time to rooting.*—Summer: About 10 weeks with soil temperatures of 25 to 30° C. Winter: About 16 weeks with soil temperatures of 20 to 25° C.

*Rooting habit.*—Fibrous and freely branching.

Plant description:

*Appearance.*—Upright and compact woody shrub. Removal of terminal apices (pinching) enhances lateral branch development. Appropriate for 9 to 30-cm containers.

*Plant height from soil level to top of plant plane.*—About 26 cm.

*Plant width/spread.*—About 20 to 25 cm.

*Growth rate.*—Moderate to rapid.

*Vigor.*—Moderate.

*Crop time.*—Starting with a rooted cutting, about 8 months are required to produce a finished flowering plant in a 13-cm container.

*Stem description.*—Diameter: About 5 mm. Internode length: About 2.5 cm. Texture: Glabrous and thornless. Color: Gray/green.

*Foliage description.*—Single, alternate, symmertical. Size (largest leaves): Length: About 9 cm. Width: About 5.25 cm. Shape: Ovate. Apex: Apiculate. Base: Cuneate. Margin: Entire. Texture: Leathery, glabrous. Petiole length: About 2.5 cm. Color: Upper surface: Close to 147A. Under surface: Close to 146A. Venation: Lighter green than leaf surface. Petiole: Lighter green than leaf surface, similar to venation.

Flower description:

*Appearance.*—Cymose inflorescences that are spherical in shape and apetalous with a tubular modified calyx and conspicuous bracts.

*Number of flowers per inflorescence.*—About 50.

*Inflorescence diameter.*—About 12 cm.

*Inflorescence height.*—About 14 cm.

*Flower diameter.*—About 3.5 cm.

*Flower height.*—About 4.5 cm.

*Bracts.*—Three showy light purple/dark pink bracts that are fused at the base and undulate with weak to moderate interveinal rugosity. Length: About 3.9 cm. Width: About 2.9 cm. Shape: Broadly ovate. Apex: Acute to apiculate. Base: Auriculate, slightly lobed. Margin: Entire. Color: Mature, upper side: close to 73A. Mature, under side: close to 73A. Venation, upper side: 144D/154C. Venation, under side: 144D/154C.

*Calyx:*—Appearance: fused and tubular 5-lobed limb; pedicel confluent with the main vein of the supporting bract. Length: About 1.7 cm. Width: About 8 mm. Color: Apex: Cream, close to 158B, with light green tinge. Base: Light green with red tinge.

*Reproductive organs.*—Stamens: Five, yellow. Pistils: One, translucent white.

Disease resistance: Resistance to known Bougainvillea diseases has not been observed to date on plants grown under commercial greenhouse conditions.

Seed production: Seed production on plants of the new Bougainvillea has not been observed.

It is claimed:

1. A new and distinct cultivar of Bougainvillea plant named 'Vera Light Purple', as illustrated and described.

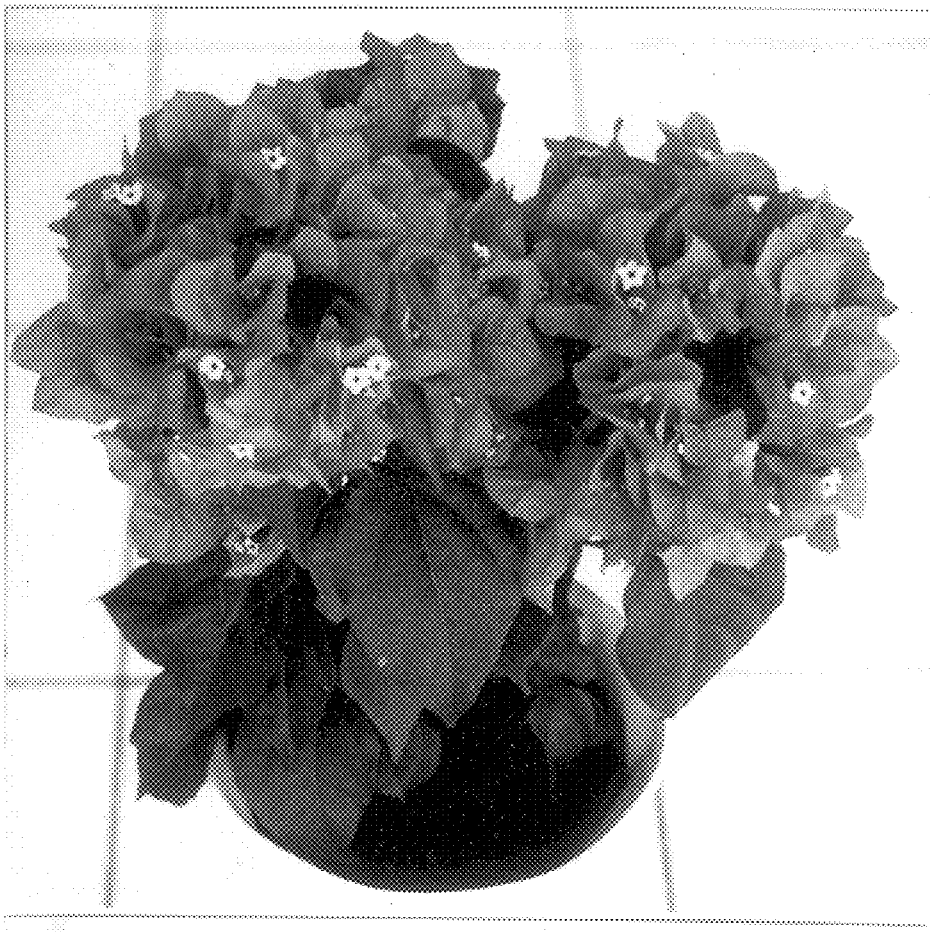
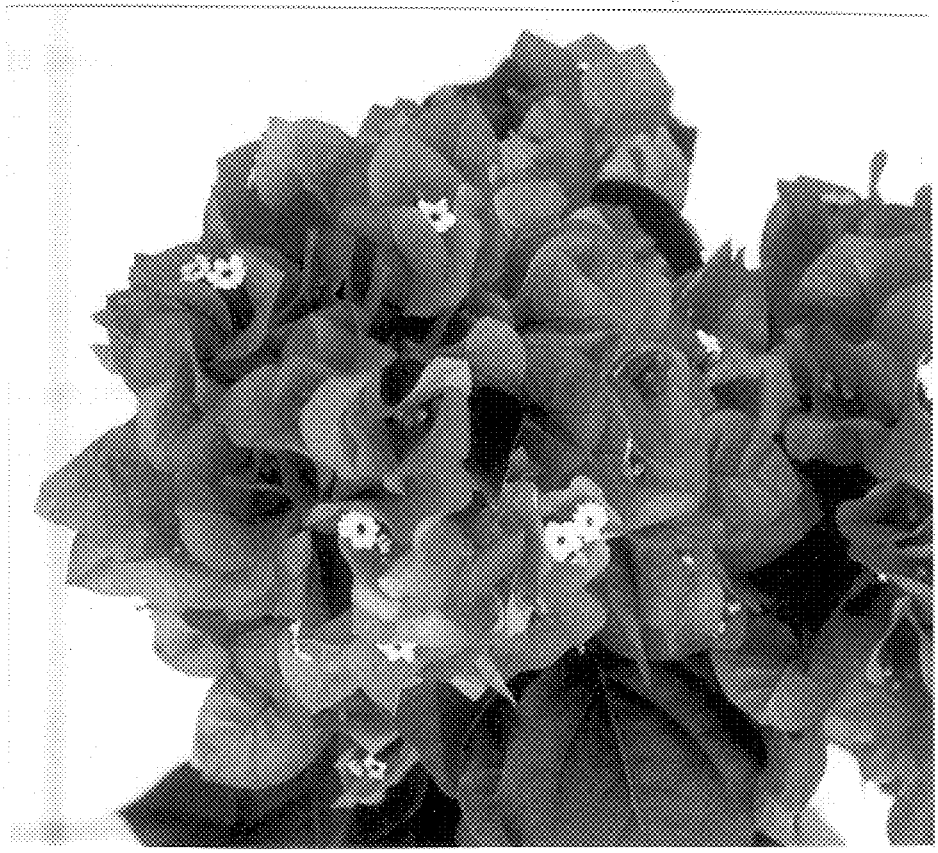

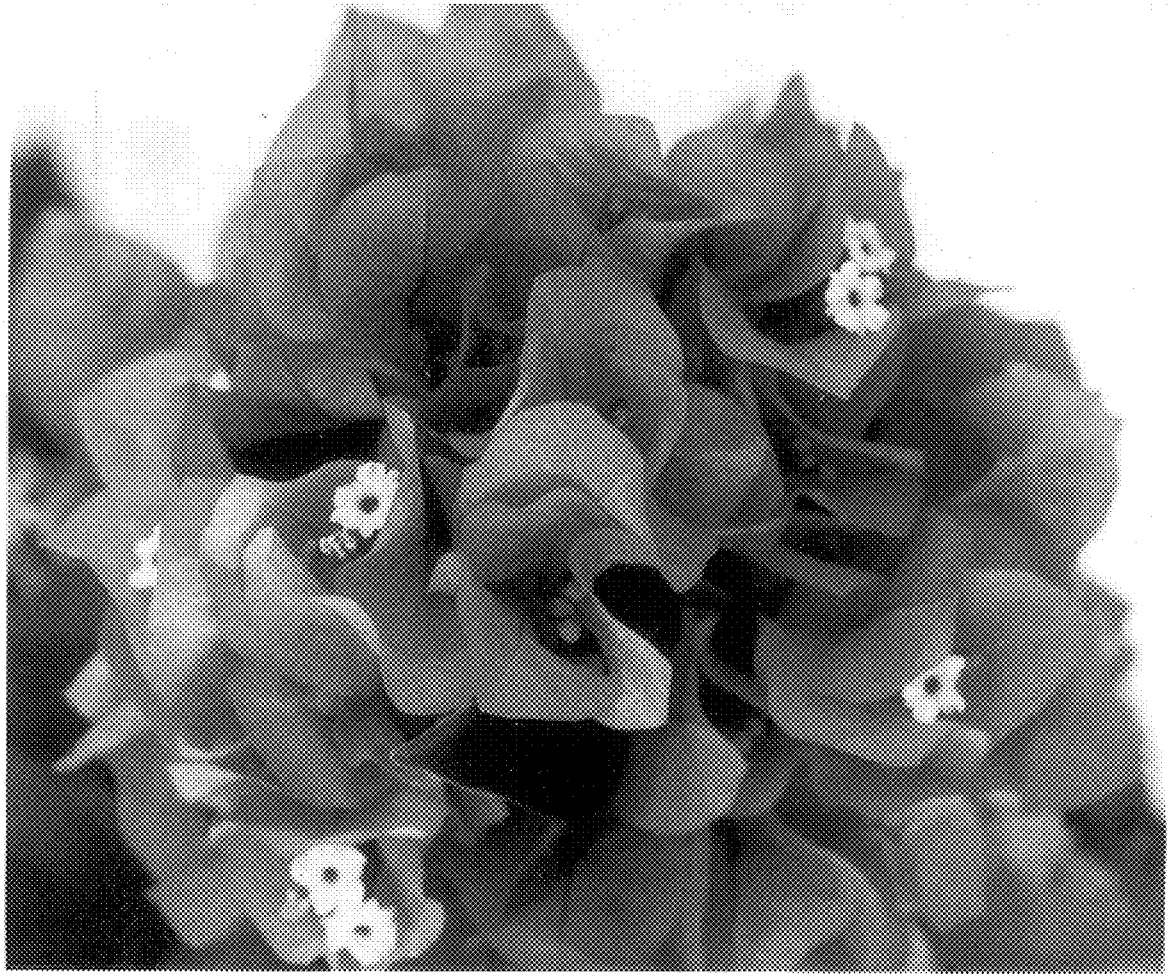

* * * * *